United States Patent
Zeqiri

(10) Patent No.: US 6,497,140 B1
(45) Date of Patent: Dec. 24, 2002

(54) CAVITATION SENSOR

(75) Inventor: Bajram Zeqiri, Teddington (GB)

(73) Assignee: The Secretary of State for Trade and Industry in Her Britannic Majesty's Government of the United Kingdom of Great Britain and Northern Ireland, London (GB)

(*) Notice: Subject to any disclaimer, the term of this patent is extended or adjusted under 35 U.S.C. 154(b) by 0 days.

(21) Appl. No.: 09/659,297

(22) Filed: Sep. 13, 2000

(30) Foreign Application Priority Data

Sep. 16, 1999 (GB) .............................................. 9921982

(51) Int. Cl.⁷ ........................ G01N 29/02; G01M 10/00
(52) U.S. Cl. .................... 73/61.61; 73/61.75; 73/61.79; 73/19.03
(58) Field of Search .............................. 73/61.61, 64.42, 73/64.53, 61.75, 19.03, 24.06, 61.79, 592

(56) References Cited

U.S. PATENT DOCUMENTS

| | | | | |
|---|---|---|---|---|
| 3,921,622 A | * | 11/1975 | Cole ......................... | 128/2 V |
| 4,083,225 A | * | 4/1978 | Day et al. ...................... | 73/19 |
| 4,236,510 A | * | 12/1980 | Hatter et al. .............. | 128/24 A |
| 4,557,137 A | * | 12/1985 | Kitamori et al. ............... | 73/24 |
| 4,644,808 A | * | 2/1987 | Lecoffre ...................... | 73/866 |
| 4,944,191 A | * | 7/1990 | Pastrone et al. .............. | 73/599 |
| 5,293,353 A | * | 3/1994 | Mestas et al. .............. | 367/157 |
| 5,852,229 A | * | 12/1998 | Josse et al. ................. | 73/24.06 |
| 5,892,144 A | * | 4/1999 | Meller et al. .............. | 73/64.42 |
| 6,111,339 A | * | 8/2000 | Ohya et al. .................. | 310/358 |
| 6,282,949 B1 | * | 9/2001 | Axelsson .................... | 73/64.53 |

* cited by examiner

Primary Examiner—Hezron Williams
Assistant Examiner—David J. Wiggins
(74) Attorney, Agent, or Firm—Thomas, Kayden, Horstemeyer & Risley LLP

(57) ABSTRACT

A cavitation sensor includes an ultrasonically absorbent coating (20) disposed around a piezoelectric element (30) and a conduit (25). The conduit (25) includes a boundary delimited by the piezoelectric element (30), while the ultrasonically absorbent coating (20) is substantially transparent to acoustic driving field frequencies. The sensor is more accurate than prior art sensors.

18 Claims, 3 Drawing Sheets

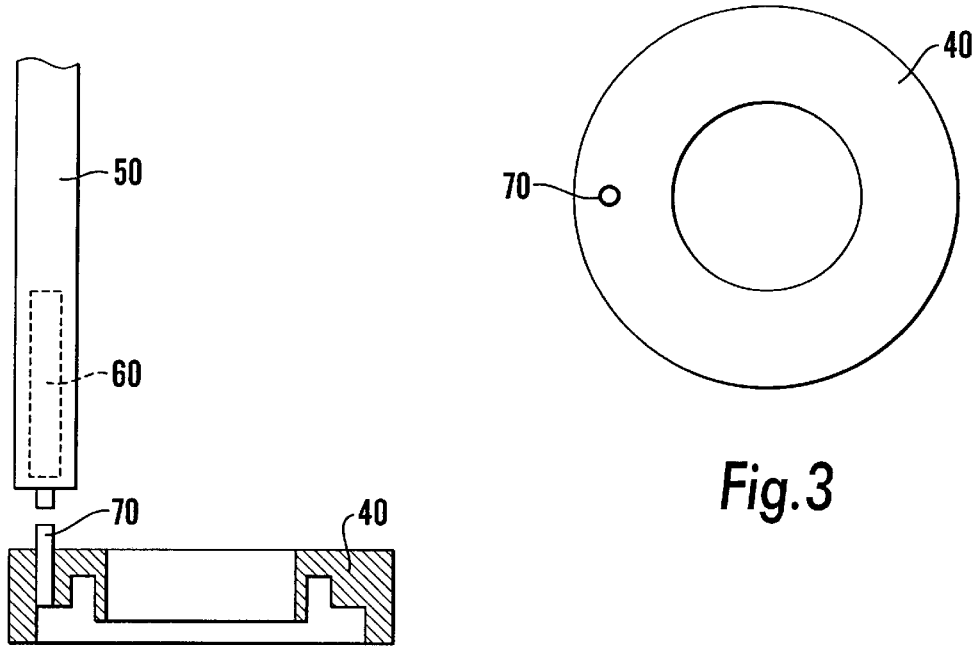
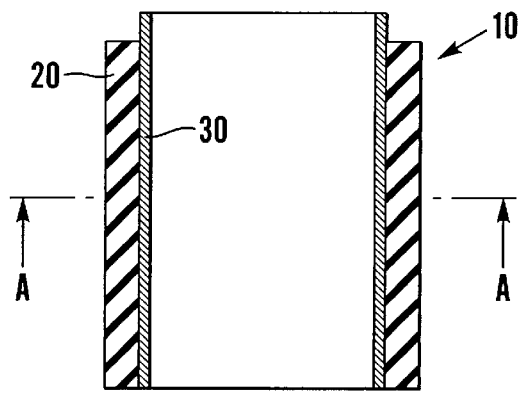
Fig.1
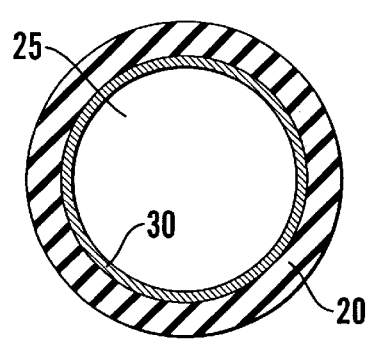
Fig.2
Fig.3

CAVITATION SENSOR

FIELD OF THE INVENTION

The present invention relates generally to the detection of cavitation events in a fluid medium and more specifically to a sensor for monitoring acoustic cavitation in ultrasonic cleaning vessels.

BACKGROUND OF THE INVENTION

Ultrasonic cleaning vessels are used throughout industry for a range of cleaning applications including sterilisation. Objects to be cleaned are placed within a bath of water containing an acoustic field generated by a single or group of transducers. The transducer will typically produce an acoustic driving field within the frequency range of about 20 kHz to 100 kHz, depending on the items to be cleaned, the degree of cleansing required and so forth.

The mechanical vibrations generated by the acoustic field induce bubble motion within the medium. This arises from small bubbles dissolved within the liquid medium, which are commonly associated with weak points within the liquid such as impurities. Cavitation is the term used to describe the oscillation, expansion and collapse of the bubbles. The oscillation and collapse of the bubbles themselves generates acoustic waves those components cover a range of frequencies dependent on details of the bubble motion but extend well into the MHz frequency range, much higher than the acoustic driving field. The bubbles can also collapse catastrophically generating shock-waves and these, along with water-jetting produced by collapse, are typical mechanisms by which ultrasonic cleaning of the component takes place. The degree of cavitation can be varied by adjusting the magnitude of the electrical drive to the transducers, thereby affecting the acoustic pressures generated in the bath.

The density of cavitating bubbles, the frequency of bubble events and the violence of the collapse is related to the effectiveness of any cleaning technique which utilises this phenomenon. The ability to measure these parameters or a combined effect of the bubble activity would enable optimisation of the driving amplitude of the transducers for a given type of cleaning vessel. It would enable the long-term performance of the cleaning vessel to be monitored and would also provide the basis of a test by which the performance of cleaning vessels could be compared.

SUMMARY OF THE INVENTION

The present invention seeks to provide a sensor for the detection of bubble events within a fluid subjected to an acoustic driving field.

According to an aspect of the present invention there is provided a cavitation sensor including an ultrasonically absorbent coating substantially enclosing a piezoelectric element and a conduit; the conduit including a boundary delimited by the piezoelectric element, the ultrasonically absorbent coating being substantially transparent to acoustic driving field frequencies.

DESCRIPTION OF THE DRAWINGS

Various embodiments of the present invention are described below, by way of example only, with reference to the accompanying drawings, in which:

FIG. 1 shows an exploded section of the preferred embodiment of cavitation sensor;

FIG. 2 shows the sectional view along line A—A of the cavitation sensor of FIG. 1;

FIG. 3 shows a plan view of a top plate of the cavitation sensor of FIG. 1;

DESCRIPTION OF THE PREFERRED EMBODIMENTS

Figure 4:
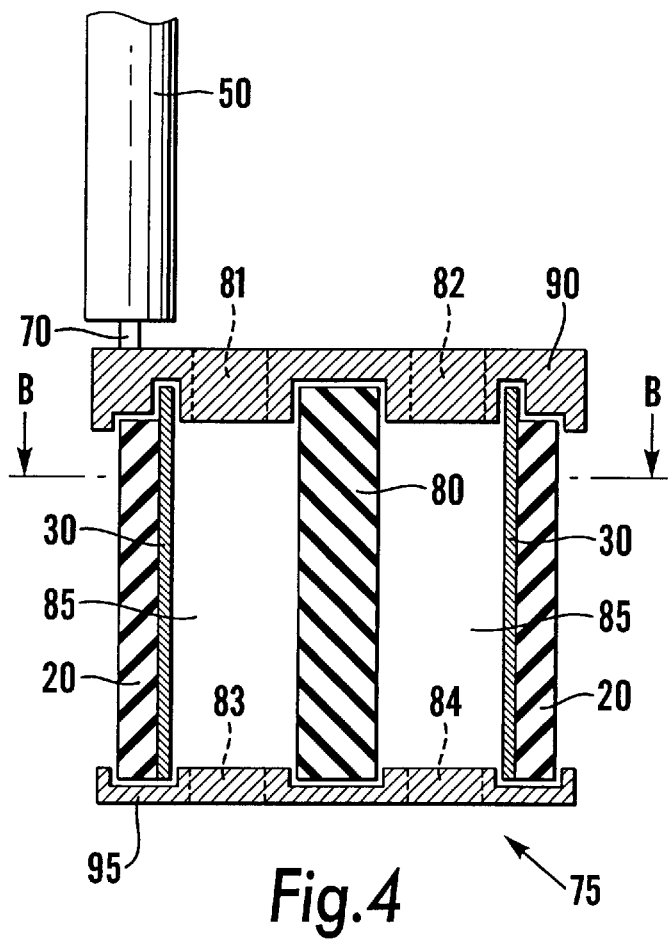
FIG. 4 shows a section of another embodiment of cavitation sensor.

With reference to FIGS. 1, 2 and 3, the embodiment of sensor 10 shown is intended to be placed within a cleaning vessel. The sensor 10 is based on a cylinder of piezoelectric material 30, the outside of which is coated with an ultrasonic absorber 20, for example made from a rubber or polymeric material such as polyurethane. For best results, the ultrasonic absorber 20 should have an acoustic impedance sufficiently well matched to that of the medium used within the cleaning vessel. The absorber 20 is very attenuating to ultrasound at frequencies above 1 MHz (even for relatively thin layers of thickness of 2 or 3 mm) but is virtually transparent to frequencies in the range 20 kHz to 80 kHz.

The advantage of these materials is that they may be used as a coating on one side of the piezoelectric sensor to shield it from acoustic signals generated by bubble collapse occurring outside the sensor cylinder. This will serve to protect the piezoelectric film and also to eliminate signals produced by cavitation bubble collapse on the sensor surface as these may dominate the response.

Running through the centre and substantially parallel to the axis of the sensor 10 is a cylindrical bore or conduit 25. When in use, that is to say when the sensor is submerged in a fluid under test, the extent of the bore defines a volume of fluid medium. The fluid medium may typically be water but could be any other fluid medium.

A top plate 40 is provided as a support frame and additionally as an interface for the connecting rod 50. Housed within the connecting rod 50 is a submersible pre-amplifier 60 to provide the necessary gain to the sensor signal that is fed through connector 70. The signal is then passed to a remote location (not shown) for processing and analysis.

Perturbations to the acoustic driving field within the fluid media caused by the introduction of the sensor must be minimised if the sensor is to be effective. It is therefore preferable to use materials which are substantially acoustically matched with the properties of the test medium, in this example water.

It has been found that materials such as polyvinylidene fluoride (pvdf) films are good piezoelectrics for this purpose. It is preferred to use piezoelectric copolymer films with a thickness less than the wavelength of acoustic frequencies in the range 40 to 50 kHz. These types of film have the desired acoustic impedance match with water.

The connecting rod 50 and the top plate 40 are preferably made from a material whose acoustic impedance match with water is reasonably close, for example a syntactic epoxy material. This type of material can be moulded and machined and can advantageously be produced with a very low density, preferably in a range between 0.5 to 0.55 g/cm$^3$. Also, syntactic epoxies have a very good acoustic impedance match to water.

When placed in a volume of water that is being subjected to an acoustic driving field, bubble events occurring within the volume provided by the cylindrical bore 25 are detected via induced responses in the piezoelectric material 30 from ultrasonic pressure waves emanating from the bubble events.

The maximum in the response is confined to a coaxial cigar shaped region extending the axial length of the sensor. The radial response decays rapidly and the rate of decay increases with increases in the driving frequency. Along the axis of the sensor the response is more-or-less constant. Although the off-axis response is much lower, it tends to increase towards the outer edge of the cylinder defined by the piezoelectric material 30 due to the inverse radial fall in pressure.

A core cylinder of acoustically transparent material may be placed in the centre of the cylinder to remove coherence and to smooth out spatial variations in the field.

Figure 5:
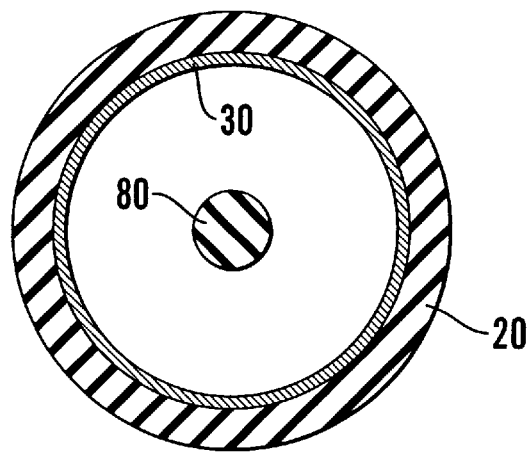
FIG. 5 shows a sectional view along line B—B of the sensor of FIG. 4.

FIGS. 4 and 5 show another embodiment of cavitation sensor. Here, an additional coaxial core of ultrasonic absorber 80 is included in the sensor 75. This core is similarly substantially transparent to the acoustic driving frequency, as is the outer coating 20. In addition to the top plate 90, a base plate 95 is also provided to give support to this sensor configuration. Vents 81, 82, 83 and 84 are included in both top plate 90 and base plate 95 to allow the fluid media access to the conduit 85.

The strong axial response to single bubble events (as discussed above) is due to the strong phase cancellation for off-axis events. Including the core 80 can remove this coherence and advantageously can help smooth out spatial variations.

Figure 6:
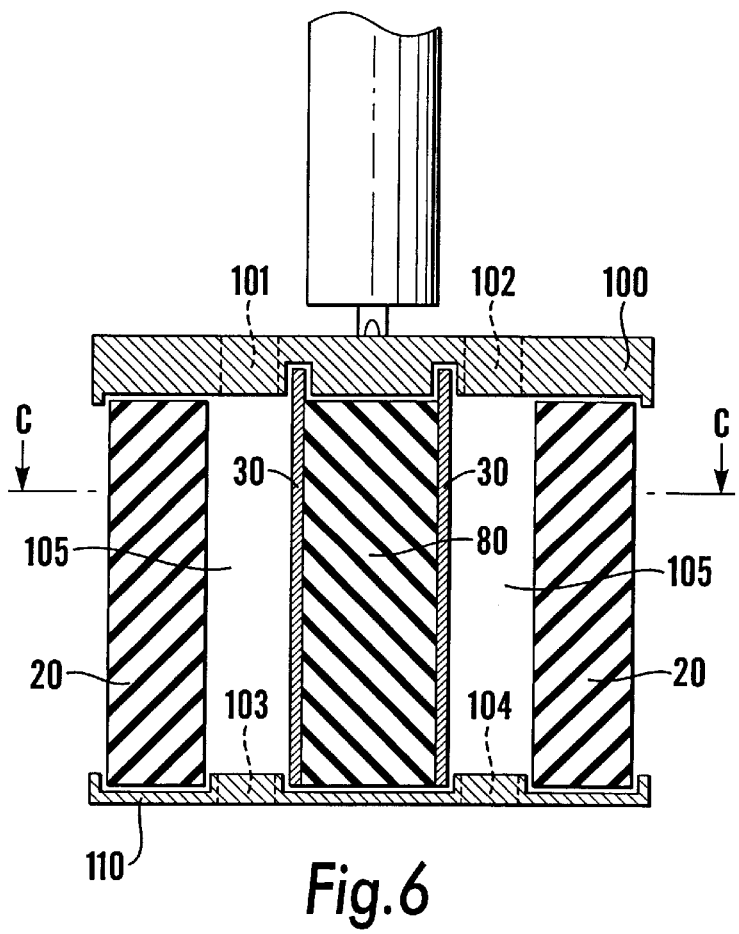
FIG. 6 shows a sectional view of another embodiment of cavitation sensor.
Figure 7:
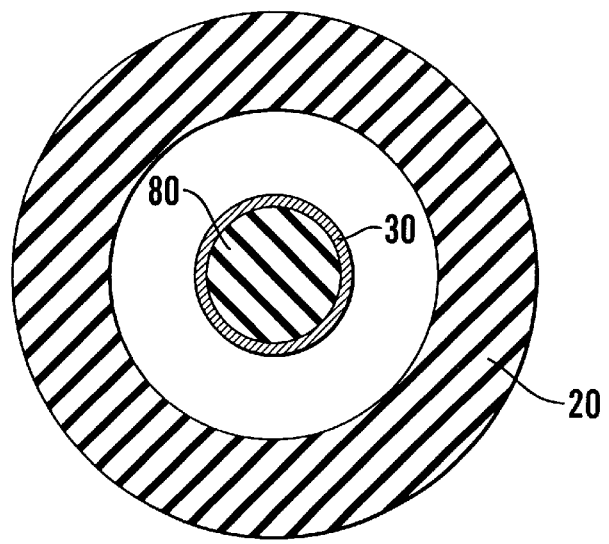
FIG. 7 shows a sectional view of the sensor of FIG. 6 along line C—C.

FIGS. 6 and 7 show another embodiment of cavitation sensor. The inner core 80 is concentric with an outer piezoelectric coating 30. The conduit 105 is bounded by a cylindrical ultrasonic absorber 20. The top plate 100 includes fluid media vents 101 and 102 with corresponding vents 103 and 104 included in the base plate 110. In this embodiment, the connecting rod 50 (which includes a preamplifier [not shown]) attaches to the sensor at a central point of the top plate.

The advantage achieved with this embodiment is that the response decays smoothly from the piezoelectric core surface to the outer absorber 20.

Piezoelectric Film Measurements

The bandwidth of the piezoelectric film needs to be as wide as possible to acquire the high frequency signals (shock-waves) produced by cavitation collapse.

A variety of different materials have been tested, and the measurements made to determine their sensitivities are described below.

To obtain figures for the sensitivity of the various piezoelectric materials available, a series of measurements were made using new and existing transducers as sources. These were driven using 5 cycle bursts at the required frequency, typically producing a peak-to-peak acoustic pressure of a few hundred kPa. Spatial distribution and acoustic pulse information was obtained over the frequency range 500 kHz to 5 MHz using a calibrated 9 $\mu$m bi-laminar membrane hydrophone. Using a substitution technique, the sensors produced from the materials investigated were then placed at the same point in the acoustic field, and the sensitivity calculated from the ratio of the voltage produced to the known acoustic pressure calculated from the hydrophone measurements. Where appropriate, corrections were made for cable loading and spatial-averaging.

Connections were made using silver conducting paint to an RG174 cable and MCX connector. The cylindrical sensor was connected to the preamplifier and placed in the acoustic far field, held vertically with the 'gap' facing the transducer. A response was seen that indicated that the device produced a signal from both sides of the cylinder, the first pulse in the time-domain trace was similar to that seen from the point sensors made previously, with the second signal being more complex, probably indicating some phase cancellation over the large area sampled. The signal was very noisy, however.

Using some varnish, the cylinder was insulated, and then covered with a nickel screening aerosol spray, with the hope that this would provide some shielding. When placed in the acoustic field, this appeared to be partially successful, with the noise levels reduced by approximately 30%.

To investigate qualitatively the response of the sensor to cavitation signals, the cylinder was placed in a tank filled with tap water, in which an acoustic transducer was operating at 750 kHz. Powers in excess of 10 W produced visible cavitation activity, shown by the sub-harmonic component (375 kHz) but, more usefully, an increase in the broadband white noise was observed in the range 1–4 MHz. No systematic trend was noted in signal levels as a function of position of the sensor relative to the beam.

Sample calculations on tested piezoelectric materials indicate a smooth increase in sensitivity up to a sharp resonance at 9 MHz, 50% higher than the values at low MHz frequencies. An off-the-shelf device of 30 mm by 15 mm was tested qualitatively in the acoustic fields as above, and produced readily-measurable signals over the range 0.5–20 MHz, expected for the thin films. Cavitation signals were also observed when placing the sensor in the tank.

In another embodiment, the film may be wrapped around an inner former, possibly made from Perspex™. With reference to the view of FIG. 2, this embodiment can be provided with an additional thin-walled core acting as the former.

It will be apparent that the features of the various embodiments can be used with all the embodiments described and falling within the scope of the appended claims.

What we claim is:

1. A cavitation sensor including an ultrasonically absorbent coating disposed around a piezoelectric element and a conduit; the conduit providing a boundary delimited by the piezoelectric element and a volume within which cavitation events are detected; wherein the ultrasonically absorbent coating absorbs ultrasonic pressure waves caused by cavitation events occurring outside the conduit, the ultrasonically absorbent coating being substantially transparent to acoustic driving field frequencies.

2. A cavitation sensor according to claim 1, wherein the sensor is substantially cylindrical in form.

3. A cavitation sensor according to claim 1, wherein the ultrasonically absorbent coating is made from a rubber or polymeric material.

4. A cavitation sensor according to claim 3, wherein the ultrasonically absorbent coating is made from polyurethane.

5. A cavitation sensor according to claim 2, wherein the ultrasonically absorbent coating is made from a rubber or polymeric material.

6. A cavitation sensor according to claim 5, wherein the ultrasonically absorbent coating is made from polyurethane.

7. A cavitation sensor including an ultrasonically absorbent coating disposed around a piezoelectric element and a conduit; the conduit including a boundary delimited by the piezoelectric element, the ultrasonically absorbent coating being substantially transparent to acoustic driving field frequencies, wherein the ultrasonically absorbent coating is attenuating to ultrasound at frequencies above around 1 MHz and is virtually transparent to frequencies in the range 20 kHz to 80 kHz.

8. A cavitation sensor according to claim 1, wherein the piezoelectric element is formed from polyvinylidene fluoride.

9. A cavitation sensor including an ultrasonically absorbent coating disposed around a piezoelectric element and a conduit; the conduit including a boundary delimited by the piezoelectric element, the ultrasonically absorbent coating being substantially transparent to acoustic driving field frequencies, wherein the piezoelectric element has a thickness less than the wavelength of acoustic frequencies in the range 40 to 50 kHz.

10. A cavitation sensor including an ultrasonically absorbent coating disposed around a piezoelectric element and a conduit; the conduit including a boundary delimited by the piezoelectric element, the ultrasonically absorbent coating being substantially transparent to acoustic driving field frequencies, wherein a core of substantially acoustically transparent material is placed in the centre of the conduit.

11. A cavitation sensor according to claim 10, wherein the ultrasonically absorbent coating is made from a rubber or polymeric material.

12. A cavitation sensor according to claim 11, wherein the ultrasonically absorbent coating is made from polyurethane.

13. A cavitation sensor according to claim 10, wherein the piezoelectric element is formed from polyvinylidene fluoride.

14. A cavitation sensor according to claim 10, wherein the piezoelectric element has a thickness less than the wavelength of acoustic frequencies in the range 40 to 50 kHz.

15. A cavitation sensor according to claim 1, wherein the an inner core is substantially concentric with an outer piezoelectric coating and the conduit is bounded by a cylindrical ultrasonic absorber.

16. A cavitation sensor including an ultrasonically absorbent coating disposed around a piezoelectric element and a conduit; the conduit including a boundary delimited by the piezoelectric element, the ultrasonically absorbent coating being substantially transparent to acoustic driving field frequencies, wherein the sensor is coated in varnish and covered with a nickel screening.

17. A cavitation sensor according to claim 10, wherein the an inner core is substantially concentric with an outer piezoelectric coating and the conduit is bounded by a cylindrical ultrasonic absorber.

18. A cavitation sensor according to claim 10, wherein the sensor is coated in varnish and covered with a nickel screening.

* * * * *